(12) United States Patent
Cai et al.

(10) Patent No.: US 8,241,567 B2
(45) Date of Patent: Aug. 14, 2012

(54) HYDROGEL COMPOSITIONS

(75) Inventors: Wensheng Cai, Chapel Hill, NC (US); Daniel Frank Berndt, Durham, NC (US); Jacob Hartsell, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 462 days.

(21) Appl. No.: 12/107,021

(22) Filed: Apr. 21, 2008

(65) Prior Publication Data
US 2008/0305007 A1  Dec. 11, 2008

Related U.S. Application Data

(60) Provisional application No. 60/913,261, filed on Apr. 20, 2007.

(51) Int. Cl.
*G01N 33/53* (2006.01)
(52) U.S. Cl. .......... 422/50; 422/420; 422/425; 422/500; 436/86; 435/14; 106/124.1
(58) Field of Classification Search .......... 422/56, 422/57, 58, 50, 420, 425, 500; 436/86; 435/14; 106/124.1
See application file for complete search history.

(56) References Cited

U.S. PATENT DOCUMENTS

| 7,432,069 | B2 * | 10/2008 | Barman et al. ............. 435/14 |
| 7,655,038 | B2 * | 2/2010 | Luthra et al. ............. 623/1.42 |
| 2005/0239155 | A1 | 10/2005 | Alarcon |
| 2005/0266038 | A1 * | 12/2005 | Glauser et al. ............. 424/423 |
| 2006/0024813 | A1 | 2/2006 | Warthoe |

OTHER PUBLICATIONS

Written Opinion and International Preliminary Report on Patentability issued in PCT Application No. PCT/US2008/061062.
International Search Report for PCT Application No. PCT/US08/61062.

* cited by examiner

*Primary Examiner* — Jill Warden
*Assistant Examiner* — Monique Cole
(74) *Attorney, Agent, or Firm* — Morgan, Lewis & Bockius LLP

(57) ABSTRACT

The invention relates to compositions comprising a hydrogel matrix, where the matrix comprises poly(ethylene glycol) dimethyacrylate (PEGDMA), an acrylate, such as methacrylic acid (MAA) and methyl methacrylate (MMA), as well as 2-hydroxy-2 methyl propiophenone (HMPP).

21 Claims, 7 Drawing Sheets

PEGDMA    MAA

-COOH

GBP
EDC/NHS

HYDROGEL COMPOSITIONS

CROSS-REFERENCE TO RELATED APPLICATIONS

The application claims priority to U.S. Provisional Application No. 60/913,261, which was filed 20 Apr. 2007 and is incorporated by reference.

BACKGROUND OF THE INVENTION

1. Field of the Invention

The invention relates to compositions comprising a hydrogel matrix, where the matrix comprises poly(ethylene glycol) dimethyacrylate (PEGDMA), an acrylate, such as methacrylic acid (MAA) and methyl methacrylate (MMA), as well as 2-hydroxy-2 methyl propiophenone (HMPP).

2. Background of the Invention

A rapidly advancing area of biosensor development is the use of periplasmic binding proteins (PBPs), to accurately determine analyte, e.g., glucose, concentrations in biological samples. In particular, glucose-galactose binding proteins (GGBPs) are being employed as biosensors to measure analyte quantities in industrial and pharmacological physiological settings. PBPs are considered to be "reagentless" and can be used in a variety of settings including measuring glucose in monitoring diabetes, measuring amino acids in other metabolic diseases, such as histidase deficiency, as well as measuring arabinose during ethanol production from corn. Wild-type GGBPs, however, may not be the most ideal candidates for measuring or determining analyte concentrations for a variety of reasons. Biosensors comprising (GGBPs would preferably be physically stable under conditions of use to generate a quantifiable signal on glucose binding. When the intended use is to monitor in vivo glucose concentrations in diabetics, the proteins would preferably be stable at physiological temperatures. Additionally, the GGBPs would preferably have enhanced stability throughout sensor manufacturing, shipping and storage, which could enable the protein and sensor materials to be fabricated at ambient temperature. This manufacturing process could include high-temperature sterilization procedures for use in a clinical setting. Exposure to high temperatures, however, may denature the protein, rendering the GGBPs useless for their intended purpose.

A implantable biosensor could be used to constantly monitor the physiological state of a subject with a medical condition such as diabetes. The ideal biosensor for monitoring the levels of a ligand or target analyte would need to be biocompatible so that the biosensor would not provoke an immune response or be subject to bio-fouling. To develop biosensors using analyte binding molecules, especially binding proteins, the binding molecules must be physically or chemically immobilized within a biosensor hydrogel in a manner that allows analyte-induced conformational change of the binding molecules. In addition, methods of chemical attachment are needed that prevent loss of the binding molecule, and provide a stable, continuous and reversible biosensor response to changing concentrations of the analyte of interest. The hydrogel matrix must be permeable to the analyte, prevent interference from other biomolecules, and be biocompatible and biostable.

Previously, binding proteins have been successfully conjugated to several natural and synthetic polymer hydrogels like alginate, crosslinked multi-arm PEG-NH$_2$ and poly(2-hydroxyethyl methacrylate) (PHEMA) and demonstrated reversible glucose binding. There are various performance deficits that hinder these materials from moving into product development. These deficits include decreased control over the rate of polymerization and swelling, poor mechanical stability, increased bioreactivity, etc.

PEG is a well-known biocompatible, nontoxic, non-immunogenic, water-soluble polymer widely used in biomaterials, biotechnology, and medicine. PEG can be modified with different functional groups useful for crosslinking with other monomers or conjugating biomolecules. There are various methods of crosslinking PEG and its derivatives into hydrogels for use in biosensor applications. Inappropriate crosslinking of PEG or PEG based derivatives, however, may produce hydrogel polymers possessing less than desirable properties for use as a biosensor.

SUMMARY OF THE INVENTION

The invention relates to compositions comprising a hydrogel matrix, where the matrix comprises poly(ethylene glycol) dimethyacrylate (PEGDMA), an acrylate, such as methacrylic acid (MAA) and methyl methacrylate (MMA), as well as 2-hydroxy-2 methyl propiophenone (HMPP).

DETAILED DESCRIPTION OF THE INVENTION

Figure 1:
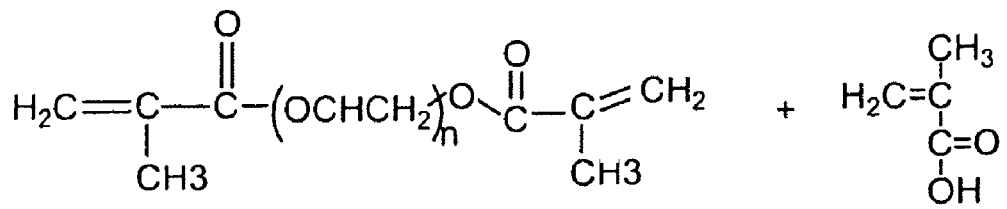
FIG. 1 depicts the chemistry scheme of crosslinking PEGDMA-MAA hydrogel and protein attachment.
Figure 1:
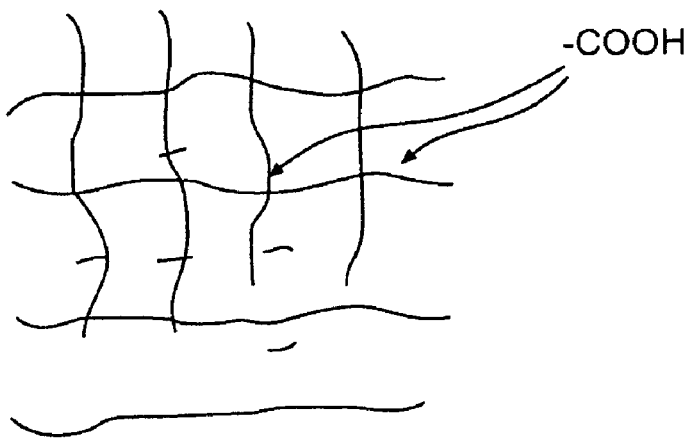
Figure 1:
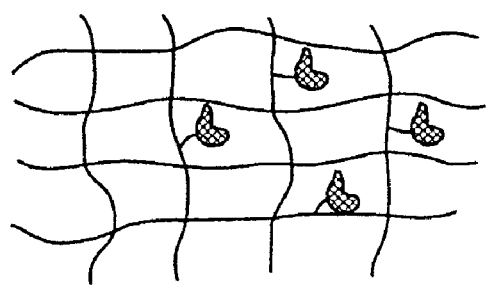

The invention relates to compositions comprising a hydrogel matrix, where the matrix comprises poly(ethylene glycol) dimethyacrylate (PEGDMA) an acrylate, such as methacrylic acid (MAA) and methyl methacrylate (MMA), as well as 2-hydroxy-2 methyl propiophenone (HMPP).

The term "hydrogel" is used to indicate a water-insoluble, water-containing material. Numerous hydrogels may be used in the present invention. The hydrogels may be, for example, polysaccharides such as agarose, dextran, carrageenan, alginic acid, starch, cellulose, or derivatives of these such as, e.g., carboxymethyl derivatives, or a water-swellable organic polymer such as, e.g., polyvinyl alcohol, polyacrylic acid, polyacrylamide, polyethylene glycol, copolymers of styrene and maleic anhydride, copolymers of vinyl ether and maleic anhydride and derivates thereof. Derivatives providing for covalently crosslinked networks are present in one embodiment of the present invention. Synthesis and biomedical and pharmaceutical applications of hydrogels based on, comprising polypeptides, have been described by a number of researchers. (See, e.g. "Biosensors Fundamentals and Applications", edited by A. D. F. Turner, I. Karube and G. S. Wilson; published from Oxford University Press, in 1988). An exemplary hydrogel matrix derived from a water-soluble, UV crosslinkable polymer comprises poly(ethylene glycol) dimethyacrylate (PEGDMA).

Any of the polymers that are to be used in the hydrogels of the present invention may be functionalized. That is, the polymers or monomers comprising the polymers may possess reactive groups such that the polymeric matrices, such as hydrogels, are amenable to chemical reactions, e.g., covalent attachment. As used herein and throughout, a "reactive group" is a chemical group that can chemically react with a second group. The reactive group of the polymer or monomers comprising the polymer may itself be an entire chemical entity or it may be a portion of an entire chemical entity, including, but not limited to single atoms or ions. Further, the second group with which the reactive group is capable of reacting can be the same or different from the reactive group of the polymer or monomers comprising the polymers. Examples of reactive groups include, but are not limited to, halogens, amines, amides, aldehydes, acrylates, vinyls, hydroxyls and carboxyls. In one embodiment, the polymers or monomers comprising the polymers of the hydrogel should be functionalized with carboxylic acid, sulfate, hydroxy or amine groups. In another embodiment of the present invention, the polymers or monomers comprising the polymers of the hydrogel are functionalized with one or more acrylate groups. In one particular embodiment, the acrylate functional groups are terminal groups. The reactive groups of the polymers or monomers comprising the polymers of the matrix may be reactive with any component of the matrix portion of the devices of the present invention, such as, but not limited to, another polymer or monomer within the matrix, a protein and an additive.

Once formed, the hydrogels used in the present invention should comprise polymers to form a polymeric hydrogel. Regardless of its application, the term "polymer" herein is used to refer to molecules composed of multiple monomer units. Suitable polymers which may be used in the present invention include, but are not limited to, one or more of the polymers selected from the group consisting of poly(vinyl alcohol), polyacrylamide, poly(N-vinyl pyrolidone), poly(ethylene oxide) (PEO), hydrolysed polyacrylonitrile, polyacrylic acid, polymethacrylic acid, poly(hydroxyethyl methacrylate), polyurethane polyethylene amine, poly(ethylene glycol) (PEG), cellulose, cellulose acetate, carboxy methyl cellulose, alginic acid, pectinic acid, hyaluronic acid, heparin, heparin sulfate, chitosan, carboxymethyl chitosan, chitin, collagen, pullulan, gellan, xanthan, carboxymethyl dextran, chondroitin sulfate, cationic guar, cationic starch as well as salts and esters thereof. The polymers of the matrix, such as a hydrogel, may also comprise polymers of two or more distinct monomers. Monomers used to create copolymers for use in the matrices include, but are not limited to acrylate, methacrylate, methyl methacrylate, methacrylic acid, alkylacrylates, phenylacrylates, hydroxyalkylacrylates, hydroxyalkylmethacrylates, aminoalkylacrylates, aminoalkylmethacrylates, alkyl quaternary salts of aminoalkylacrylamides, alkyl quaternary salts of aminoalkylmethacrylamides, and combinations thereof. Polymer components of the matrix may, of course, include blends of other polymers.

In one embodiment, the hydrogel is comprised of PEGDMA. PEGDMA is commercially available in a variety of molecular weights. For example, PEGDMA is available from at least Aldrich Chemical Co. (Milwaukee, Wis. ISA) and from Polysciences, Inc. (Warrington, Pa., USA) and can be synthesized in an assortment of molecular weights. In one embodiment, the molecular weight of PEGDMA used in the hydrogels of the present invention is from about 400 to about 4000. In a more specific embodiment, the molecular weight of the PEGDMA in the hydrogels is about 1000.

In another embodiment, the hydrogels comprise PEGDMA and at least one acrylate. As used herein, the term acrylate is well understood in the art. Specifically, acrylates are compounds, including but not limited to polymers, comprising the acrylic group ($H_2C=CH-C(=O)$). Examples of acrylates include, but are not limited to, acrylic acid, ethyl acrylate, methacrylic acid, methyl methacrylic acid and acrylamides. FIG. 1 shows the chemical formula of both PEGDMA and MAA which can be used together in one specific embodiment. In another specific embodiment the hydrogels comprise more than one acrylate. In a more specific embodiment, the hydrogels comprise a mixture of methacrylate and methyl methacrylate.

The polymers used in the matrices can be modified to contain nucleophilic or electrophilic groups. Indeed, the polymers used in the present invention may further comprise polyfunctional small molecules that do not contain repeating monomer units but are polyfunctional, i.e., containing two or more nucleophilic or electrophilic functional groups. These polyfunctional groups may readily be incorporated into conventional polymers by multiple covalent bond-forming reactions. For example, PEG can be modified to contain one or more amino groups to provide a nucleophilic group. Examples of other polymers that contain one or more nucleophilic groups include, but are not limited to, polyamines such as ethylenediamine, tetramethylenediamine, pentamethylenediamine, hexamethylenediamine, bis-(2-hydroxyethyl)amine, bis-(2-aminoethyl)amine, and tris-(2-aminoethyl)amine. Examples of electrophilic groups include but are not limited to, succinimide esters, epoxides, hydroxybenzotriazole esters, oxycarbonylimidazoles, nitrophenyl carbonates, tresylates, mesylates, tosylates, carboxylates, and isocyanates. In one embodiment, the composition comprises a bis-amine-terminated poly(ethylene glycol).

The polymers should be capable of crosslinking, either physically or chemically, to form the hydrogel. Physical crosslinking includes, but is not limited to, such non-chemical processes as radiation treatment such as electron beams, gamma rays, x-rays, ultraviolet light, anionic and cationic treatments. The crosslinking of the polymers may also comprise chemical crosslinking, such as covalent crosslinking. For example, a chemical crosslinking system may include, but is not limited to, the use of enzymes, which is well-known in the art. Another example of the chemical covalent crosslinking comprises the use of peroxide. Chemical crosslinking may occur when a crosslinking reagent reacts with at least two portions of a polymer to create a three-dimensional network. Covalent crosslinking may also occur when multifunctional monomers are used during the crosslinking process. For example, an acrylate monomer may be polymerized with a bifunctional acrylate monomer to form a crosslinked polymer. Any crosslinking reagent will be suitable for the present invention provided the crosslinking reagent will at least partially dissolve in water or an organic solvent and can form the crosslinked polymer. For example, if the polymer is an amine-terminated PEG, the crosslinking reagent should be capable of reacting with the PEG-amine groups and be substantially soluble in water.

If the polymers to be crosslinked are functionalized with nucleophilic groups, such as amines (primary, secondary and tertiary), thiols, thioethers, esters, nitrites, and the like, the crosslinking reagent can be a molecule containing an electrophilic group. Examples of electrophilic groups have been described herein. Likewise, if polymers to be crosslinked are functionalized with electrophilic groups, the crosslinking reagent can be a molecule containing a nucleophilic group. It is understood that one skilled in the art can exchange the nucleophilic and electrophilic functional groups as described above without deviating from the scope of the present embodiment. It is also understood that proteins, if present in the hydrogel, can provide the requisite nucleophilic and electrophilic functional groups. For example, the nucleophilic and electrophilic functional groups may be present as naturally occurring amino acids in the protein, or may be introduced to the protein using chemical techniques described herein.

Other general methods for preparing or crosslinking polymers to form matrices such as hydrogels are well known in the art. For example, Ghandehari H., et al., J. Macromol. Chem. Phys. 197: 965 (1996); and Ishihara K, et al., Polymer J., 16: 625 (1984), all of which are hereby incorporated by reference, report the formation of hydrogels.

In one embodiment, the matrix comprises poly(ethylene glycol) dimethacrylate (PEGDMA) and at least one acrylate, such as methacrylic acid (MAA) and/or methyl methacrylate (MMA). The ratio of PEGDMA to acrylate may vary among specific embodiments. In one embodiment the ration of PEGDMA:acrylate can range from about 10:90 mol % to about 90:10 mol %. In one specific embodiment, the ratio of PEGDMA:acrylate is about 20:80 mol %. In another specific embodiment, the ratio of PEGDMA, acrylate is about 21:79 mol %. In another specific embodiment, the ratio of PEGDMA:acrylate is about 23:77 mol %. In another specific embodiment, the ratio of PEGDMA:acrylate is about 25:75 mol %. In another specific embodiment, the ratio of PEGDMA:acrylate is about 27:73 mol %. In another specific embodiment, the ratio of PEGDMA:acrylate is about 29:71 mol %. In another specific embodiment, the ratio of PEGDMA:acrylate is about 30:70 mol %. In another specific embodiment, the ratio of PEGDMA:acrylate is about 35:65 mol %. In another specific embodiment, the ratio of PEGDMA:acrylate is about 40:60 mol %. In another specific embodiment, the ratio of PEGDMA:acrylate is about 42:58 mol %. In another specific embodiment, the ratio of PEGDMA:acrylate is about 44:56 mol %. In another specific embodiment, the ratio of PEGDMA:acrylate is about 46:54 mol %. In another specific embodiment, the ratio of PEGDMA:acrylate is about 48:52 mol %. In another specific embodiment, the ratio of PEGDMA:acrylate is about 50:50 mol %. In the above embodiments, the acrylate can be MAA or MMA alone, or some combination thereof, such that the ratio of PEGDMA:total acrylate falls within the embodied range.

The hydrogel matrices of the present invention may or may not comprise additional components such as, but not limited to, photoinitiators. Initiators, such as 2-Hydroxy-2 methyl propiophenone (HMPP), may also be present in various concentrations in the hydrogel. Examples of additional initiators include but are not limited to, Benzophenone, 4-Methylbenzophenone, 4-Phenylbenzophenone, Benzildimethylketal, Isopropylthioxanthone (mixture of 2-/4-isomers), Isopropylthioxanthone 2-isomer, Ethyl-4-dimethylaminobenzoate (EPD), 2-Methyl-1-[4-(methylthio)-phenyl]-2-morpholino-propanone-1,2-Hydroxy-2-methyl-phenyl-propan-1-one, Mixtures of 2,4,6-Trimethylbenzophenone and 4-Methylbenzophenone, Mixtures of 2,4,6-Trimethylbenzophenone, 2-Methyl-benzophenone, 3-Methylbenzophenone and 4-Methylbenzophenone, TPO-Diphenyl(2,4,6-Trimethylbenzyl) phosphine oxide and Ethyl(2,4,6-Trimethylbenzoyl)phenyl phosphinate, to name a few. For example, photoinitiators may be present in concentrations from about 0.10% to about 5% total volume. In one embodiment, the photoinitiator is HMPP and is present in concentrations of from about 0.1% to about 1%. In a specific embodiment, the photoinitiator is present at least about 0.20% total volume. In a specific embodiment, the photoinitiator is present at least about 0.25% total volume. In a specific embodiment, the photoinitiator is present at least about 0.27% total volume. In a specific embodiment, the photoinitiator is present at least about 0.29% total volume. In a specific embodiment, the photoinitiator is present at least about 0.30% total volume. In a specific embodiment, the photoinitiator is present at least about 0.31% total volume. In a specific embodiment, the photoinitiator is present at least about 0.33% total volume. In a specific embodiment, the photoinitiator is present at least about 0.35% total volume. In a specific embodiment, the photoinitiator is present at least about 0.37% total volume. In a specific embodiment; the photoinitiator is present at least about 0.39% total volume. In a specific embodiment, the photoinitiator is present at least about 0.40% total volume. In a specific embodiment, the photoinitiator is present at least about 0.41% total volume. In a specific embodiment, the photoinitiator is present at least about 0.45% total volume. In a specific embodiment, the photoinitiator is present at least about 0.49% total volume.

The hydrogel matrices of the present invention may further comprise proteins, such that the protein is coated with or entrapped within the hydrogel matrix. Any protein or polypeptide can be coated or entrapped with the hydrogel matrix. In one embodiment, the proteins are periplasmic binding proteins, which are a well-known class of bacterial proteins involved in the transport of compounds through the periplasmic space of bacteria. In one specific embodiment, the periplasmic binding protein is a glucose-galactose binding protein (GGBPs). For the purposes of the present invention, a glucose-galactose binding protein (GGBP) includes any protein that possesses these structural characteristics described herein and can specifically bind to glucose and/or galactose. FIG. 1 also depicts the GGBP covalently attached to portions of the cross-linked hydrogel.

Glucose-galactose binding protein is a member of the well-known class of periplasmic binding proteins, where these proteins are characterized by their three-dimensional configuration (tertiary structure), rather than the amino acid sequence (primary structure) of the protein. Each member of the class possesses a characteristic lobe-hinge-lobe motif. See Dwyer, M. A. and Hellinga, H. W., Curr. Opin. Struct. Biol., 14:495-504 (2004), which is hereby incorporated by reference. The PBPs will normally bind an analyte specifically in a cleft region between the lobes of the PBP. Furthermore, the binding of an analyte in the cleft region will then cause a conformational change to the PBP that makes detection of the analyte possible. In general, the conformational changes to the PBP upon specific analyte binding are characterized by the two lobe regions to bend towards each other around and through the hinge region. See Quiocho, F. A. and Ledvina, P. S., Mol. Microbiol. 20; 17-25 (1996), which is incorporated by reference. Examples of PBPs include, but are not limited to, glucose-galactose binding protein (GGBP), maltose binding protein (MBP), ribose binding protein (RBP), arabinose binding protein (ABP), dipeptide binding protein (DPBP), glutamate binding protein (GluBP), iron binding protein (FeBP), histidine binding protein (HBP), phosphate binding protein (PhosBP), glutamine binding protein (QBP), leucine binding protein (LBP), leucine-isoleucine-valine-binding protein (LIVBP), oligopeptide binding protein (OppA), or derivatives thereof, as well as other proteins that belong to the families of proteins known as periplasmic binding protein like I (PBP-like I) and periplasmic binding protein like II (PBP-like II).

In particular, the hydrogels of the present invention may comprise modified of GCBPs. A "modified protein" is used to mean a protein can be created by addition, deletion or substitution of one or more amino acids in the primary structure (amino acid sequence) of a reference protein or polypeptide. The terms "protein" and "polypeptide" are used interchangeably herein. The reference protein need not be a wild-type protein, but can be any protein that is targeted for modification for the purposes of increasing thermal stability. Thus, the reference protein may be a protein whose sequence was previously modified over a wild-type protein. Of course, the reference protein may or may not be the wild-type protein from a particular organism. Furthermore, the term "wild-type protein" includes the wild-type protein with or without a "leader sequence." Examples of GGBPs that can be used in matrices of the present invention include but are not limited to those GGBPs described in U.S. application Ser. No. 11/738,442 (Pre-Grant Publication No. 2008/0044856), which is incorporated by reference. One particular example of a modified GGBP that may be useful in the present invention is described in Pre-Grant Publication No. 2008/0044856 is a GGBP termed "SM4" which is described in Example 4, at paragraph 125 and table I. Other examples of GCBPs for use in the present invention include, but are not limited to, those that are described in U.S. Pat. No. 6,855,556, U.S. patent application Ser. No. 10/776,643 (Pre-Grant Publication No. 2005/0014290) all of which are incorporated by reference. Other examples of additional GGBPs that can be used in the present invention include those described in U.S. application Ser. No. 10/686,529, filed Oct. 16, 2003 and published as United States Published Application No. 2004/0118681. One particular example of a modified GGBP that may be useful in the present invention is described in Pre-Grant Publication No. 2004/0118681 is a GGBP termed "W183C" which is the *E. coli* wild type GGBP with a single W183C mutation.

Proteins can be covalently attached to or non-covalently entrapped or encapsulated within the hydrogel matrix. The covalent attachment of the protein to the hydrogel should not interfere with the binding of the protein to the target ligand. Furthermore, the covalent attachment of the protein to the hydrogel should be resistant to degradation. The coupling of the protein to the hydrogel can be accomplished in any number of ways. For example, coupling reactions between the hydrogel and protein include, but are not limited to, diazonium coupling, isothiocyano coupling, hydrazide coupling, amide formation, disulfide coupling, maleic anhydride coupling, thiolactone coupling, and dichlotriazine coupling. These coupling reactions between two functional groups are well documented, and are considered well known to those skilled in the art. For example, an amino functional group in a binding molecule can be covalently coupled to a carboxyl functional group of one or more components of a hydrogel using coupling agents such as 1-ethyl-3-(3-dimethylaminopropyl)carbodiimide hydrochloride (EDC) or dicyclohexylcarbodiimide (DCC). It is understood that the amino and carboxyl functional groups of the binding molecule and one or more components of the hydrogel as described above can be transposed without deviating from the scope of the embodiment. In one specific embodiment, a glucose-galactose binding protein can be covalently attached to the PEGDMA-MAA hydrogel using N-ethyl-N'-(3-dimethlaminopropyl) carbodiimide hydrochloride/N-hydroxysuccimide (EDC/NHS) chemistry. The resultant compositions show greatly improved in vivo stability compared with compositions constructed using other hydrogel materials.

The hydrogel matrices of the present invention may further comprise additional components such as, but not limited to, heparin. In one specific example, a monomer used in the present invention can be modified to incorporate heparin. For example, incorporation of heparin into the hydrogel coating formulation may involve the chemical modification of heparin sodium salt. The ring-opening reaction of the epoxide glycidyl methacrylate (GMA) is carried out with $K_2CO_3$ in $H_2O$ (pH=10.5) at 40° C. over 16 hours with GMA in 25-fold excess. The crude reaction product is precipitated into 25× ethanol to remove any non-reacted GMA, filtered, re-suspended in $diH_2O$ and then lyophilized. Direct nucleophilic addition ($S_N2$ attack) by the $RNH_2$ of heparin will take place at the least substituted epoxide carbon yielding the methacrylated heparin. The synthesized heparin-methacrylate (HP-MA) monomer can then be used as part of the hydrogel matrix formulation to create a "heparin containing hydrogel matrix."

The heparin-containing hydrogel matrices of the present invention can be used as an additional hydrogel layer on top of, for example, a non-heparin-containing hydrogel layer. Alternatively, the heparin-containing hydrogel matrices of the present invention can be used alone and may also comprise proteins, such a glucose-galactose binding protein.

In general, the amount of HP-MA used in the hydrogel formulations of the present invention will replace or substitute for the amount of PEGDMA in the preparations. As discussed above, in one embodiment of the non-heparin-containing hydrogels, the ratio of PEGDMA:acrylate can range from about 10:90 mol % to about 90:10 mol %. In heparin-containing hydrogels, ratio of PEGDMA to Acrylate to HP-MA can range from about 20:25:55 mol % to about 60:25:15. In other embodiments, however, the ratio of acrylate can also vary. In one specific embodiment, the ratio of PEGDMA:acrylate:HP-MA is about 60:25:15 mol %. In another specific embodiment, the ratio of PEGDMA:acrylate:HP-MA is about 30:25:45 mol %. In another specific embodiment, the ratio of PEGDMA:acrylate:HP-MA is about 50:25:25 mol %. The heparin-containing hydrogel matrices of the present invention may also comprise any of the other components presented herein, including but not limited to photoinitiators.

As mentioned above, proteins may be entrapped within a hydrogel matrix, which may then be used as an implantable device. As used herein, the term "entrap" and variations thereof is used interchangeably with "encapsulate" and is used to mean that the protein is immobilized within or on the constituents of the matrix. The matrix can be in any desirable form or shape including one or more of disk, cylinder, patch, nanoparticle, microsphere, porous polymer, open cell foam, and combinations thereof, providing it permits permeability to analyte. The matrix may also prevent leaching of the protein.

The matrix may be prepared from biocompatible materials or incorporates materials capable of minimizing adverse reactions with the body. Adverse reactions for implants include inflammation, protein fouling, tissue necrosis, immune response and leaching of toxic materials. Such materials or treatments are well known and practiced in the art, for example as taught by Quinn, C. P.; Pathak, C. P.; Heller, A.;

Hubbell, J. A. Biomaterials 1995, 16(5), 389-396, and Quinn, C. A. P.; Connor, R. E.; Heller, A. Biomaterials 1997, 18(24), 1665-1670.

The hydrogel matrices of the present invention can be applied to devices as a coating. The hydrogel matrix can also coat or entrap a protein, and the protein/hydrogel composition can be applied to a device. In one embodiment, the device comprises a needle tip or cannula. In one specific embodiment, the hydrogel matrix is coated onto a needle or cannula, prior to the addition of the protein. In another specific embodiment, the protein is added to the hydrogel matrix before or at the same time that the matrix is coated is onto a needle or cannula. To that end, one example of a method of coating the hydrogel to the devices of the present invention comprises applying the compositions of the present invention to the device and subsequently curing the composition under a Hg lamp, with wavelength of >360 nm, for about 15 seconds.

The hydrogel can be coated from within, by sending UV light down the fiber optic to cure the hydrogel from the inside out. Another way to cure the hydrogel would be to expose the outer surface of the hydrogel to UV light and cure the hydrogel from the outside inwards. Thus, in one embodiment, the hydrogel is cured in place after being applied to the tip of, for example, a fiber or needle tip. In another embodiment, the hydrogel is cured prior to the application or addition of any protein. Methods of applying proteins to a cured hydrogels are described in United State Published Application Nos. 2005/0113657 and 2005/0113658, which are incorporated by reference.

Figure 2:
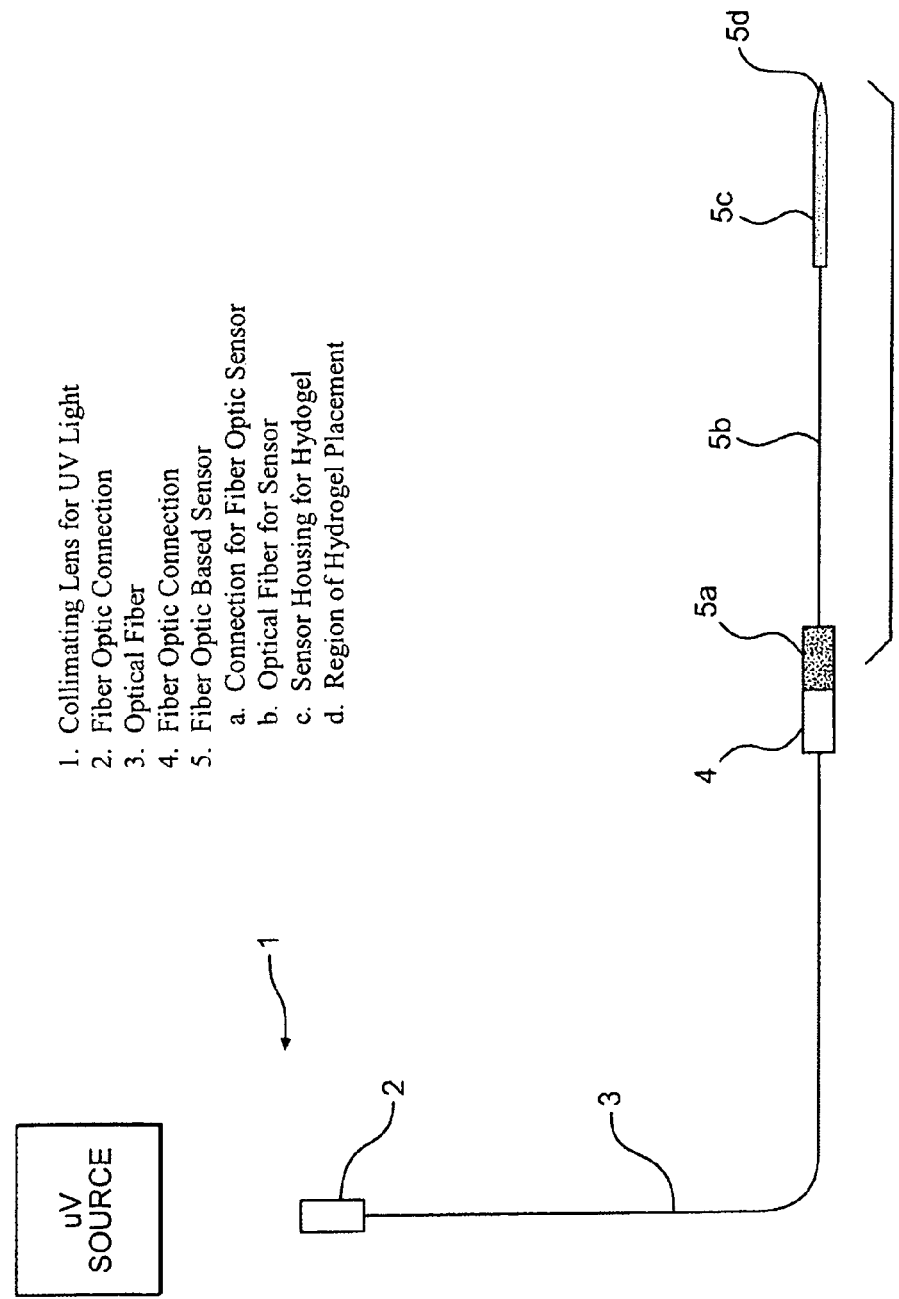
FIG. 2 depicts a schematic representation of UV polymerization of PEGDMA-M in matrix on fiber tip by UV light down optical fiber.

One example of such a device that comprises a hydrogel matrix, a protein and a needle or cannula is a biosensor, capable of generating a detectable signal in response to an analyte. The hydrogel matrix of the present invention would, among other things, serve as a coating to increase the biocompatibility of devices, such that the devices are implantable in a subject, such as a mammal, human or non-human primate, etc. The matrix permits light from optical sources or any other interrogating light to or from the reporter group to pass through the biosensor. When used in all in vivo application, the biosensor will be exposed to a substantially physiological range of analyte and determination or detection of a change in analyte concentration would be desired, whereas the determination or detection includes continuous, programmed, and episodic detection means. Thus, in one embodiment of the present invention, the envisaged in vivo biosensor comprises at least one protein in an analyte permeable entrapping or encapsulating hydrogel matrix such that the protein provides a detectable and reversible signal when the protein is exposed to varying analyte concentrations. The detectable and reversible signal can be related to the concentration of the analyte. A schematic representation of a device comprising the hydrogels of the present invention is shown in FIG. 2.

The biosensors would be capable of providing continuous monitoring of glucose for the entire time they are implanted in the subject. In one embodiment, the present invention relates to the biosensors remaining implanted in the subject for at least or up to 2, 4, 6, 8, 10, 12, 14, 16, 18, 20 or 22 hours and the implanted biosensors provide continuous blood glucose monitoring. In one embodiment, the present invention relates to the biosensors remaining implanted in the subject for at least or up to one day (24 hours) and the implanted biosensors provide continuous blood glucose monitoring. In another embodiment, the biosensors remain implanted in the subject for at least or up to two days (48 hours) and the implanted biosensors provide continuous blood glucose monitoring. In another embodiment, the biosensors remain implanted in the subject for at least or up to three days (72 hours) and the implanted biosensors provide continuous blood glucose monitoring. In another embodiment, the biosensors remain implanted in the subject for at least or up to four days (96 hours) and the implanted biosensors provide continuous blood glucose monitoring. In another embodiment, the biosensors remain implanted in the subject for at least or up to five days (120 hours) and the implanted biosensors provide continuous blood glucose monitoring. In another embodiment, the biosensors remain implanted in the subject for at least or up to six days (144 hours) and the implanted biosensors provide continuous blood glucose monitoring. In another embodiment, the biosensors remain implanted in the subject for at least or up to seven days (168 hours) and the implanted biosensors provide continuous blood glucose monitoring. In another embodiment, the biosensors remain implanted in the subject for at least or up to eleven days (264 hours) and the implanted biosensors provide continuous blood glucose monitoring.

The present invention therefore also relates to methods of making the hydrogels and devices of the present invention. In one specific embodiment, the hydrogels are prepared within a small volume and in a confined space such as a fiber tip that would allow for control of polymerization and providing specific hydrogel properties. In one specific embodiment of this invention, PEGDMA with molecular weight of ~1000 is photocopolymerized with MAA on the tip of an optical fiber by using UV light conducted through the fiber. The resultant copolymerization is extremely fast and provides a cured and functional hydrogel within seconds. The hydrogel prepared by this method also shows improved mechanical strength and little measurable swelling in a physiological buffer solution.

The coated devices of the present invention are useful in a variety of methods and applications, such as industrial processes, and as components of biosensors to detect, monitor or measure analyte quantities in a sample. Thus the present invention also relates to methods of using the hydrogel matrices and devices described herein. Biosensors are devices capable of providing specific quantitative or semi-quantitative analytical information using a biological recognition element, such as a GGBP or a modified GGBP, which is combined with a transducing (detecting) element. Examples of analytes include, but are not limited to, carbohydrates such as monosaccharides, disaccharides, oligosaccharides and polysaccharides, proteins, peptides and amino acids, including, but not limited to, oligopeptides, polypeptides and mature proteins, nucleic acids, oligonucleotides, polynucleotides, lipids, fatty acids, lipoproteins, proteoglycans, glycoproteins, organic compounds, inorganic compounds, ions, and synthetic and natural polymers. In one embodiment, the analyte is a carbohydrate. In particular, the carbohydrate analyte may be a sugar, such as glucose, galactose or ribose. More particularly, the analyte may be glucose.

The analyte is measured in a sample. As used herein, a sample can be any environment that may be suspected of containing the analyte to be measured. Thus, a sample includes, but is not limited to, a solution, a cell, a body fluid, a tissue or portion thereof, and an organ or portion thereof. When a sample includes a cell, the cell can be a prokaryotic or eukaryotic cell, for example, an animal cell. Examples of animal cells include, but are not limited to, insect, avian, and mammalian such as, for example, bovine, equine, porcine, canine, feline, human and nonhuman primates. The scope of the invention should not be limited by the cell type assayed. Examples of biological fluids to be assayed include, but are not limited to, blood, urine, saliva, synovial fluid, interstitial fluid, cerebrospinal fluid, lymphatic fluids, bile and amniotic fluid. The scope of the methods of the present invention should not be limited by the type of body fluid assayed. The terms "subject" and "patient" are used interchangeably herein and are used to mean an animal, particularly a mammal, more particularly a human or nonhuman primate.

The samples may or may not have been removed from their native environment. Thus, the portion of sample assayed need not be separated or removed from the rest of the sample or from a subject that may contain the sample. For example, the blood of a subject may be assayed the glucose without removing any of the blood from the patient. For example, an implantable biosensor may, in some embodiments, be implanted into or below the skin of a mammal's epidermal-dermal junction to interact with the interstitial fluid, tissue, or other biological fluids. Examples of biosensors that may be used in the present invention include those devices described in the United States Non-Provisional Application claiming priority to Application No. 60/913,258, the filing date of which was 21 Apr. 2008 and the priority date of which was 20 Apr. 2008, entitled "BIOSENSORS FOR MEASURING ANALYTES IN THE INTERSTITIAL FLUID", which is incorporated by reference. In one specific embodiment, biosensor is implanted in the skin at any depth. In another specific embodiment, biosensor is implanted in the skin at a depth of less than about 2 mm. In a more specific embodiment, biosensor is implanted in the skin at a depth of less than about 1 mm. In an even more specific embodiment, biosensor is implanted in the skin at a depth of less than about 0.8 mm. Information from the implant to the patient may be provided, for example, by telemetry, visual, audio, or other means known in the art, as previously stated.

Of course, the sample may also be removed from its native environment. Furthermore, the sample may be processed prior to being assayed. For example, the sample may be diluted or concentrated; the sample may be purified and/or at least one compound, such as an internal standard, may be added to the sample. The sample may also be physically altered (e.g., centrifugation, affinity separation) or chemically altered (e.g., adding an acid, base or buffer, heating) prior to or in conjunction with the methods of the current invention. Processing also includes freezing and/or preserving the sample prior to assaying.

The devices of the present invention may, in general, comprise (i) an optical conduit having a proximal end and a distal end, and a (ii) a sensing element in optical proximity to the distal end of the optical conduit. The sensing element would comprise a protein and at least one reporter group. The protein and/or label may be entrapped within the hydrogel matrices of the present invention. Example of reporter groups that are attached to the proteins of the present invention are well known and described in at least U.S. application Ser. No. 11/738,442 (Pre-Grant Publication No. 2008/0044856), U.S. Pat. No. 6,855,556 and U.S. patent application Ser. No. 10/776,643 (Pre-Grant Publication No. 2005/0014290, all of which are incorporated by reference. Additional reporter groups include, but are not limited to, those compounds that are described in United States Patent Publication No. 2006/0280652, published 14 Dec. 2006 and PCT Publication No. WO 2006/025887, which are incorporated by reference.

The optical conduit, which may vary in length from approximately 0.1 cm to 5 meters, couples light into and out of an optical system and into and out of the sensing element. For example, the optical conduit may be a lens, a reflective channel, a needle, or an optical fiber. The optical fiber may be either a single strand of optical fiber (single or multimode) or a bundle of more than one fiber. In one embodiment, the bundle of fibers is bifurcated. The fiber may be non-tapered or tapered so that it can penetrate the skin of a patient.

An optical system may be connected to the proximal end of the optical conduit. The optical system consists of a combination of one or more excitation sources and one or more detectors. It may also consist of filters, dichroic elements, a power supply, and electronics for signal detection and modulation. The optical system may optionally include a microprocessor.

The optical system interrogates the sample either continuously or intermittently by coupling one or more interrogating wavelengths of light into the optical conduit. The one or more interrogating wavelengths then pass through the optical conduit and illuminate the sensing element. A change in analyte concentration may result in a change of the wavelength, intensity, lifetime, energy transfer efficiency, and/or polarization of the luminescence of the reporter group, which is a part of the sensing element. The resulting changed luminescence signal passes back through the optical conduit to the optical system where it is detected, interpreted, and stored and/or displayed. In certain embodiments, the optical system comprises multiple excitation sources. One or more of these sources may be modulated to permit dynamic signal processing of the detected signal, thereby enhancing signal-to-noise and detection sensitivity. Modulation may also be used to reduce power consumption by the device or to increase the lifetime of the sensing element by minimizing undesirable phenomena such as photobleaching. The optical system can also include one or more electromagnetic energy detectors that can be used for detecting the luminescence signal from the reporter and optional reference groups as well as for internal referencing and/or calibration. The overall power consumption of the optical system is kept small to permit the device to be operated using battery power.

The following examples are illustrative and are not intended to limit the scope of the invention described herein.

EXAMPLES

Example 1

In Vivo Performance of PEGDMA-MAA Sensors

Figure 3:
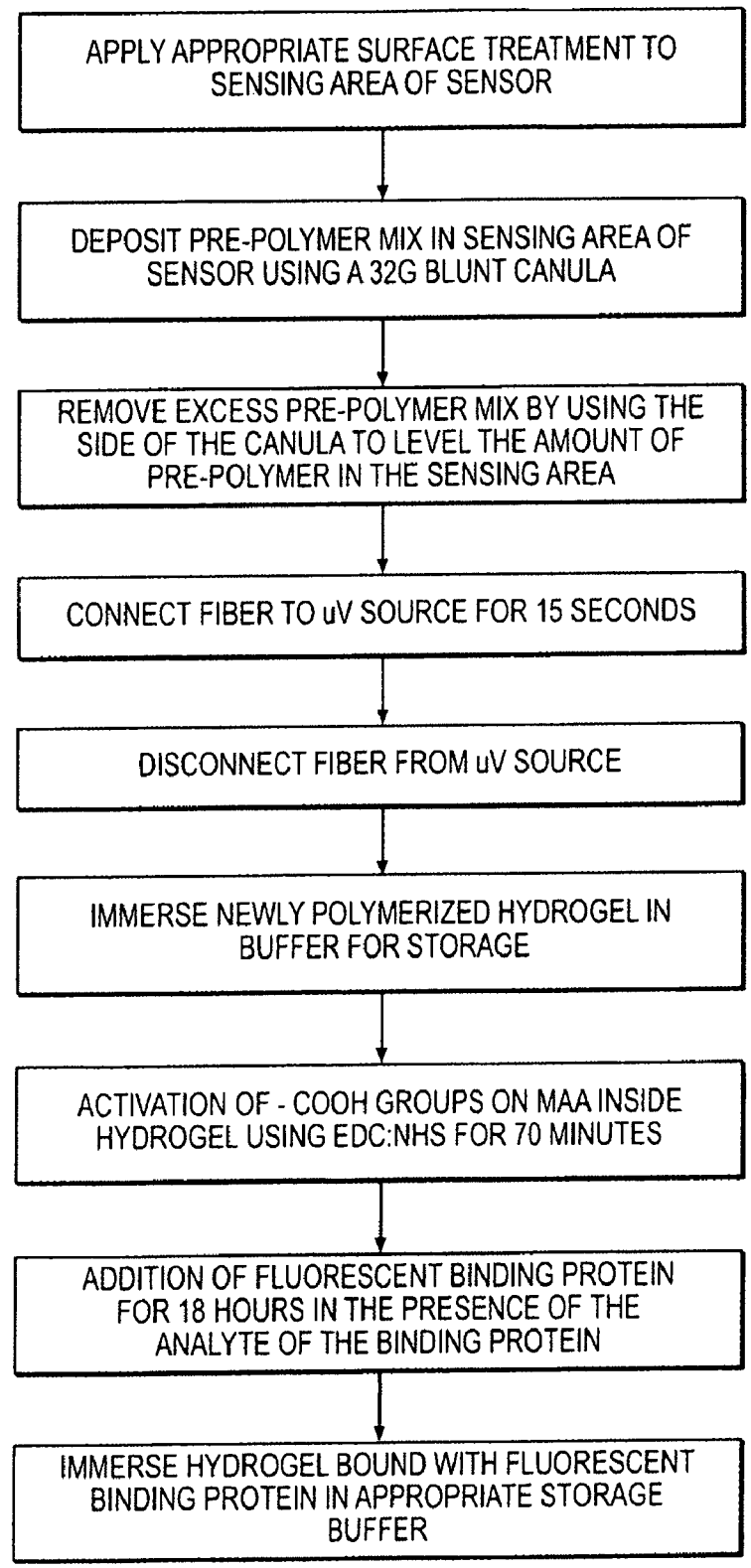
FIG. 3 depicts general PEGDMA-MAA fiber sensor fabrication process.

In this experiment, the modified GGBP termed "W183C," as described in United States Published Application 2004.0118681, was used. Typical PEGDMA-MAA fiber sensors containing Acrylodan-W183C-GBP were fabricated with the process depicted in FIG. 3. PEGDMA, MAA and photo-initiator HMPP (2-Hydroxy-2 methyl propiophenone) were mixed in appropriate molar ratios and deposited on optical fiber tips. PBS was used as the reaction solvent forming the hydrogel with the HMPP added last after all reagents have been dissolved and thoroughly mixed. The fibers were first treated with a 5N sulfuric acid wash followed by a 45 minute treatment of Acrylopropyltrimethosilane (AcPTMS). The hydrogel was completely cured under a Hg lamp with (>360 nm wavelength) for ~15 seconds (the jumper set-up to deliver ~50-65 mW/cm$^2$ to the end of the jumper) followed by immediate storage in 0.01M MES pH=0.65.

Tables 1 and 2 show the constituents of the hydrogel formulations dubbed as PEG 4 and PEG 5.

TABLE 1

PEG 5 Formulation

| | mol % MAA to PEG 77.0% PEGDMA | Wt % Monomer to Water 23.2% | | | Total Vol 1770 |
|---|---|---|---|---|---|
| | 60:40 | HMPP | PBS | MAA | Tot H20 |
| Density | 1.1 | 1.08 | 1 | 1.01 | 1 |
| FW | 1154 | 164 | 18 | 86.09 | 18 |
| microliters | 500 300 | 5 | 1183 | 81.6 | 1383 |
| milligram | 330 | 5.4 | 1183.123 | 82.418 | 1383.12 |
| micromols | 0.2860 | 0.0305 | 65.7290 | 0.9574 | 76901.62 |

TABLE 2

PEG4 Formulation

| | mol % MAA to PEG 56.0% PEGDMA | Wt % Monomer to Water 14.2% | | | Total Vol 3253 |
|---|---|---|---|---|---|
| | 60:40 | HMPP | PBS | MAA | Tot H20 |
| Density | 1.1 | 1.08 | 1 | 1.01 | 1 |
| FW | 1154 | 164 | 18 | 86.09 | 18 |
| microliters | 632 379.2 | 10 | 2572 | 39.2 | 2825 |
| microgram | 417.12 | 10.8 | 2572.101 | 39.604 | 2824.90 |
| micromols | 0.3615 | 0.0610 | 142.8945 | 0.4600 | 157064.49 |

Figure 4:
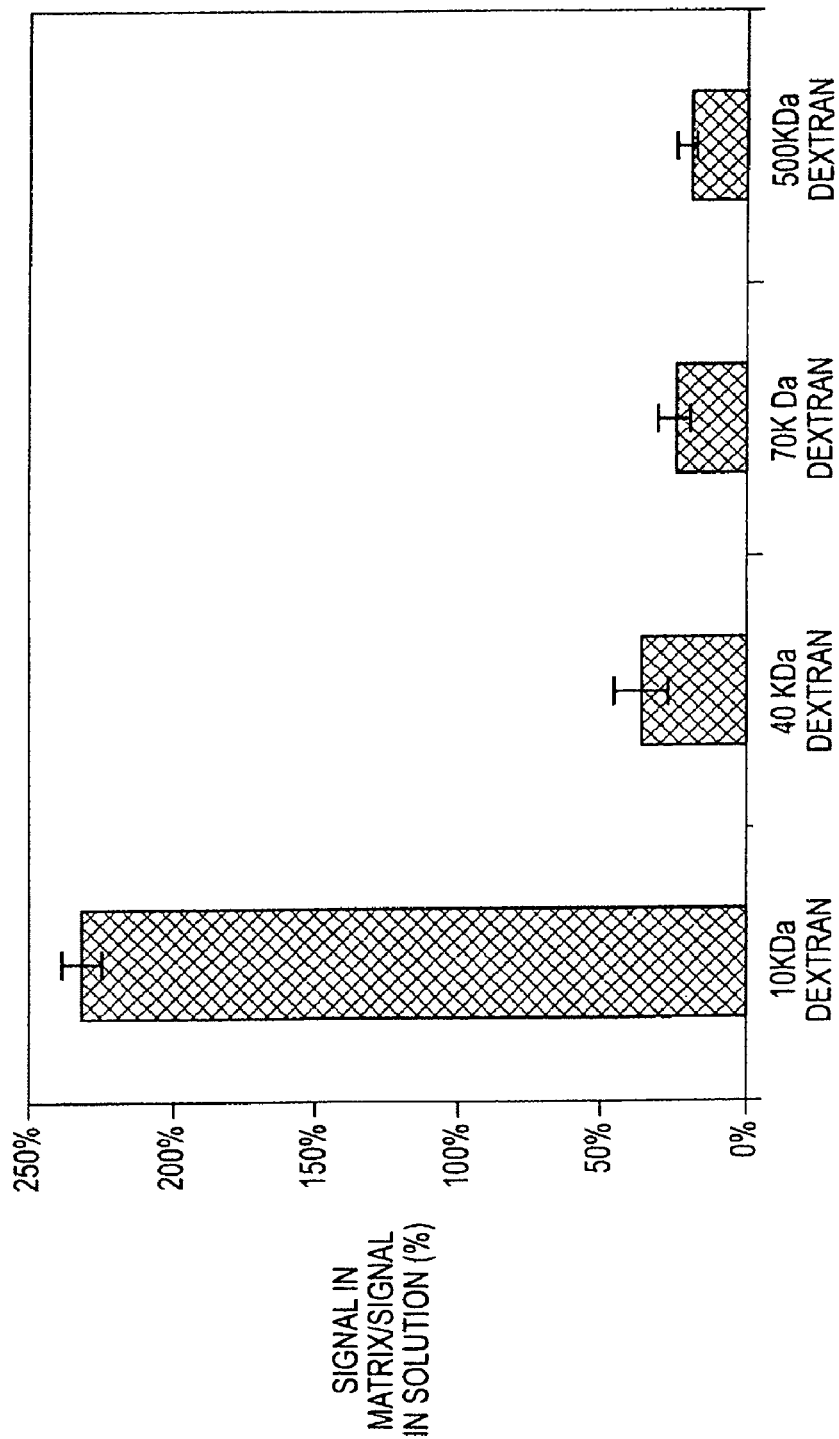
FIG. 4 depicts optical fiber sensors fabricated with PEGDMA-MAA sensors have controllable molecules exclusion toward different molecular size dextran.

GBP protein was then coupled to the hydrogel matrix using the two-step EDC/NHS activation method, which is well-known in the art. Briefly, the sensors were soaked in EDC/NHS solution for about 70 minutes to activate the carboxy groups (—COOH). Next, mutant GBP (W183C) was infused into the sensor matrix over an 18-hour period, to allow coupling of the protein to the hydrogel matrix. The PEGDMA-MAA hydrogel matrix has controllable permeability to different molecular size dextran molecules (FIG. 4), which may be beneficial for excluding large biomolecules, such as enzymes and other proteins, from entering the sensor matrix and degrading the sensing chemistry.

In one animal experiment, all fabricated sensors, termed as PEG3' sensors, tracked glucose changing in swine after 52 hours implantation. The average loss in sensor signal intensity in vivo after 52 hours was 57% versus a 35% loss in intensity for in vitro controls. This loss in sensitivity is significantly lower than the intensity loss in alginate sensors. In other animal experiments, 13 of total 15 PEG3' fabricated sensors tracked glucose changes in swine more than 72 hours after implantation. The average loss in sensor signal intensity in vivo was 65% versus a 35% loss in intensity for in vitro controls.

Example 2

Improved PEGDMA-MAA Sensors In Vivo Performance

The photo-polymerization and protein immobilization procedure described in example 1 was further optimized. The UV power was increased 4 times by removing UV light filter and protein immobilization was conducted in presence of 30 mM glucose for better protection of protein binding activity during coupling process. The post-polymerization rinse and protein infusion buffer pH was also optimized for protein favorable pH. The PEGDMA-M sensors fabricated with the optimized process have improved sensor signal (F0), dynamic range (QR) and here are termed as PEG 4 (PEGDMA:MAA ratio of 44:56 mol %) sensors.

In the animal experiments, 14 of total 15 PEG 4 sensors tracked glucose changes after implanted for 72 hours in swine. The average 72 hours sensor signal intensity loss in vivo was 53% versus 23% for in vitro controls.

Similar experiments were carried out using either the SM4 (Pre-Grant Publication No. 2008/0044856) mutant GGBP or the W183C mutant GGBP, both of which were encapsulated with the PEG5 hydrogel formulation. Table 3 shows that a large majority of the implanted sensors were able to track glucose up to and beyond 7 days after implantation.

TABLE 3

| | Day 1 MPE(stdev) | Day 5 96 hrs in-vivo MPE(stdev) | Day 8 168 hrs in-vivo MPE(stdev) | Day 11 240 hrs in-vivo MPE(stdev) | Day 12 264 hrs in-vivo MPE(stdev) |
|---|---|---|---|---|---|
| PEG5 W183C | 16.3(8.2) N = 23 | 14.9(11.7) N = 23 | 17(7.5) N = 22 | 37.7(25) N = 6 | 13(3) N = 3 |
| PEG5 SM4 | 14.4(6.7) N = 22 | 15.4(9.1) N = 21 | 21.3(9.2) N = 20 | 36.5(52) N = 8 | 25.1(6.3) N = 6 |
| Average MPE Tracking sensors | 15.4(7.5) | 15.2(10.4) | 19(8.6) | 37(41.2) | 21(8) |
| Total Tracking | 45/47 | 44/47 | 44/47 | 14/16 | 9/12 |

Example 3

Production of a Biosensor with a Hydrogel Comprising Methacrylated Heparin

Incorporation of heparin into a hydrogel was accomplished by chemically modifying heparin sodium salt. The ring-opening reaction of the epoxide glycidyl methacrylate (GMA) was carried out with $K_2CO_3$ in $H_2O$ (pH 10.5) at 40° C. over 16 hours with GMA in 25-fold excess. The crude reaction product was precipitated into 25× ethanol to remove any non-reacted GMA, then filtered and re-suspended in $diH_2O$ and subsequently lyophilized. The synthesized heparin-methacrylate (HP-MA) monomer was then used as a $2^{nd}$ layer formulation on top of a first hydrogel coating on a needle, with the free vinylic protons incorporated into the polymer backbone.

A pre-coating is first applied using a 1-5 second "dip", preferably a 3-second dip to a highly wettable surface. A 5-10 second ultraviolet light exposure, preferably a 6 second exposure, polymerized the coating, causing the coating rapidly adhere to both the device surface and the 1st layer hydrogel surface (with GGBP present). Based on a qualitative-type toluidine blue assay, the adhesion of the UV coating 2nd layer formulation to the cannula was adequate for further experimentation. The toluidine blue assay also shows that the adhesion of the UV coating 2nd layer formulation to the hydrogel was adequate for further experimentation. The resulting coating was uniform and provided good coverage on the device and the 1st layer hydrogel.

Example 4

Figure 5:
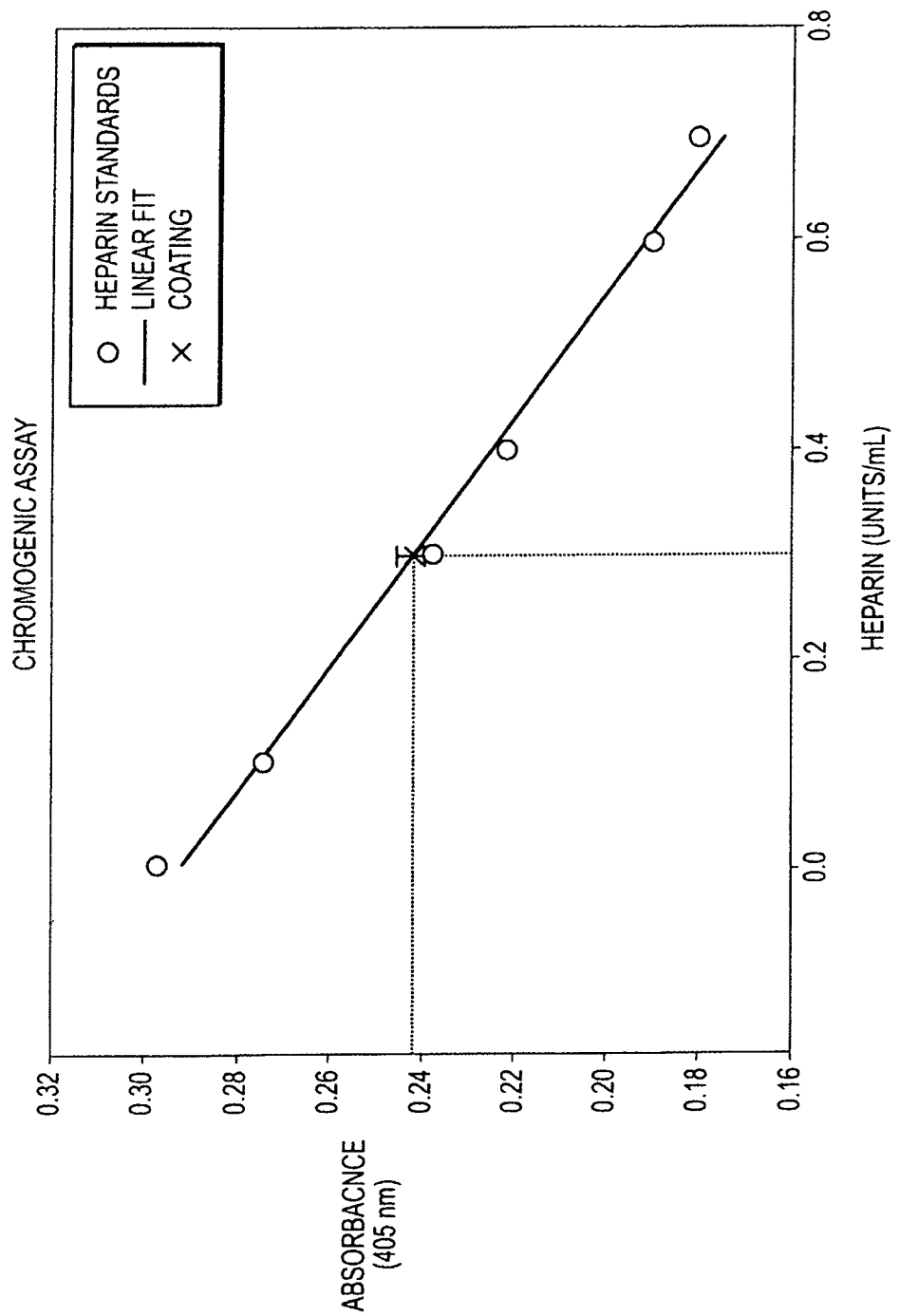
FIG. 5 depicts a summary of the heparin load for a UV-cured $2^{nd}$ layer formulation, where the second layer comprises methacrylated heparin.

In Vitro Glucose Response of a Biosensor with a Hydrogel Comprising Methacrylated Heparin Using a heparin activity assay, which utilizes a chromogenic substrate, the incorporation of heparin into the hydrogel was measured at 251.03 mU/cm2, which corresponds to a heparin load of 0.0176 µg. This level of activity was observed on day 1 after the coating process and persists through, at minimum, day 21 after application. The heparin activity was measured on sensors stored at room temperature and at 37° C. and shown to be consistent (FIG. 5 and Table 4).

TABLE 4

|  | Measured (U/mL) | Heparin Activity (mU) | Heparin Load (µg) | Coverage (mU/cm$^2$) |
| --- | --- | --- | --- | --- |
| Day 1 | 0.318 | 3.978 | 0.0196 | 280.01 |
| Day 4 | 0.250 | 3.125 | 0.0155 | 219.96 |
| Day 9 | 0.294 | 3.676 | 0.0182 | 258.75 |
| Day 13 (96 hrs @ 37° C.) | 0.302 | 3.776 | 0.0187 | 265.78 |
| Day 21 (12 days @ 37° C.) | 0.262 | 3.277 | 0.0162 | 230.66 |
| Average UV Coating | 0.285 | 3.566 | 0.0176 | 251.03 |

Figure 6:
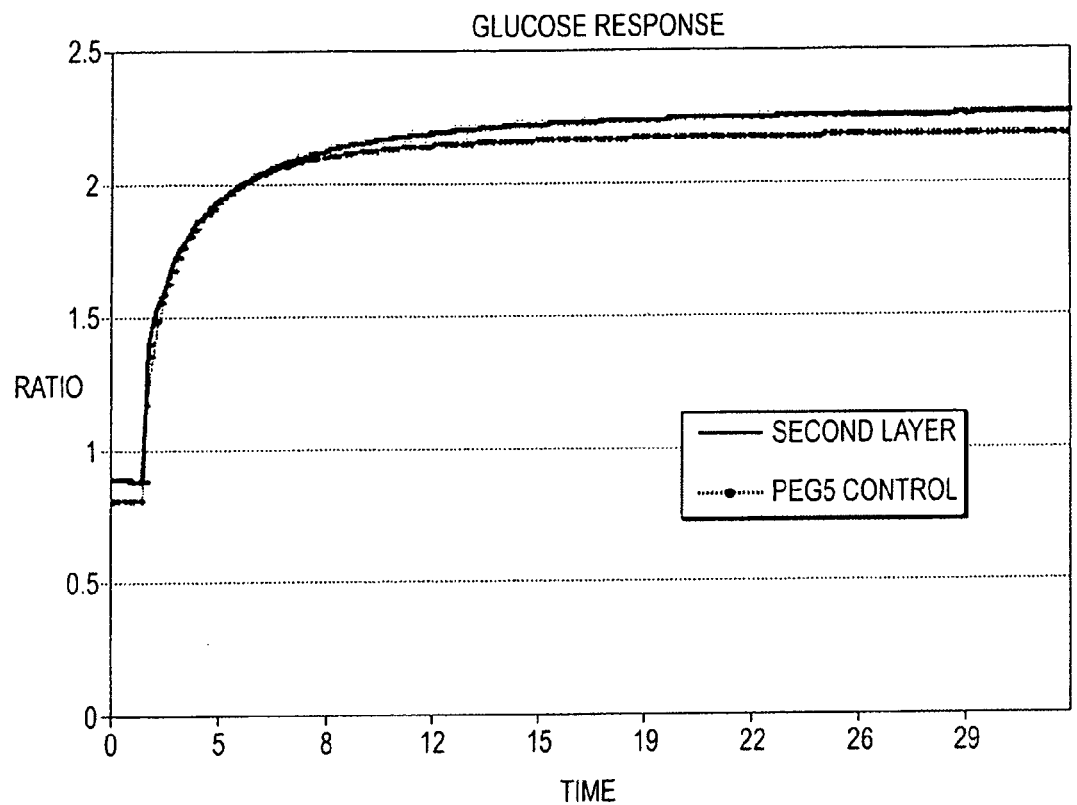
FIG. 6 depicts the additional 30 seconds required for the UV-cured $2^{nd}$ layer coating (comprising methacrylated heparin) to reach a 90% maximum glucose response, compared to a control sensor with only one hydrogel layer. An additional 78 seconds are required to reach a 95% maximum glucose response compared to the controls.

The sensor's glucose response time was not dramatically affected by the application of the outer coating. The time required to reach a 90% maximum glucose response observed in a PEG5-modified GGBP (termed SM4) sensor, without a second hydrogel coating ("uncoated sensors"), was measured at 5.5 minutes. The composition designated "PEG5" has a ratio of PEGDMA:MAA of 23:77 mol %. The time required for sensors coated with an additional 2nd hydrogel layer comprising heparin ("coated sensor") to reach an observed 90% maximum glucose response was measured at 6.0 minutes. The time required to reach a 95% maximum glucose response observed in an uncoated PEG5-SM4 sensor was measured at 8.1 minutes. The time required for UV sensors coated with an additional hydrogel layer comprising heparin to reach a 95% maximum glucose response was measured at 9.3 minutes (FIG. 6).

Example 5

Figure 7:
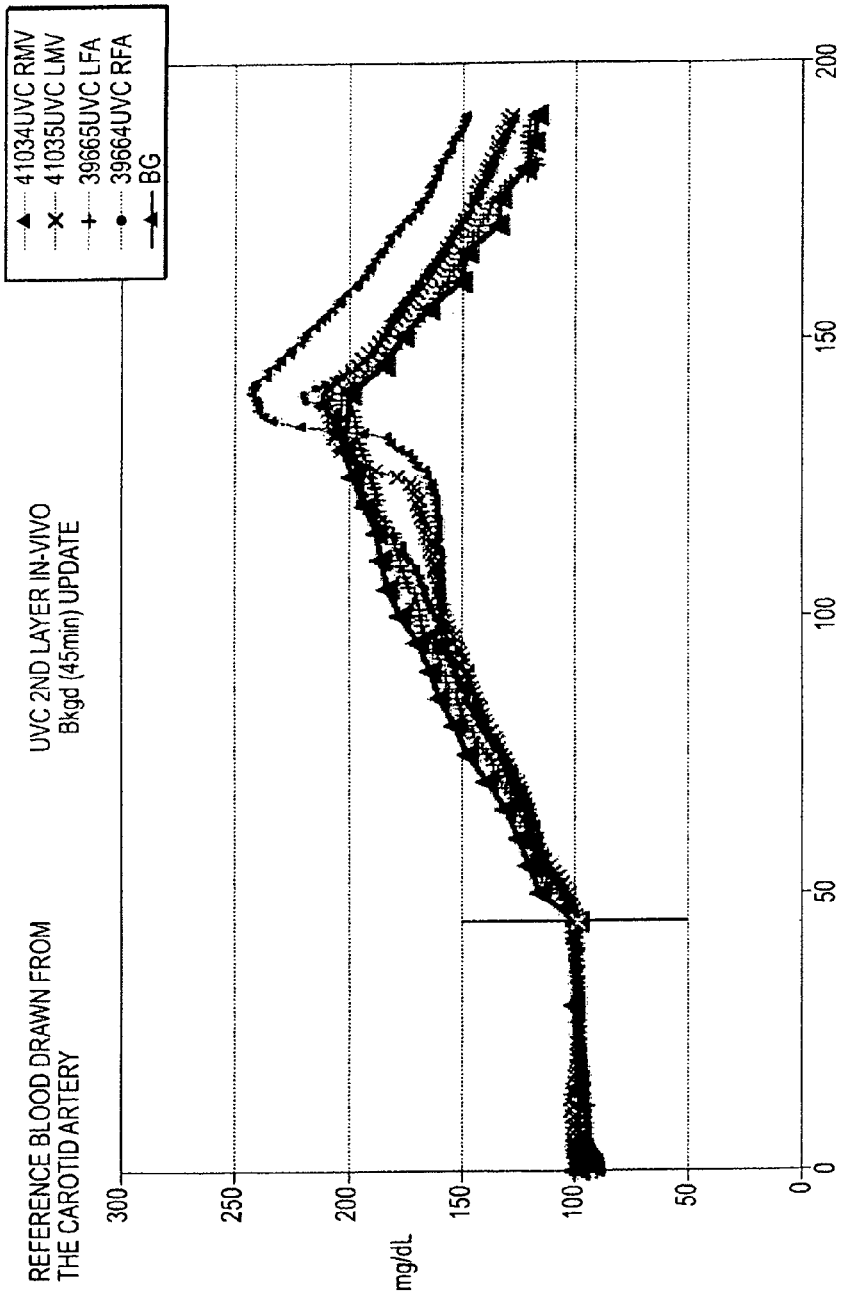
FIG. 7 depicts in vivo glucose excursion with a 25-gauge needle that houses a biosensor comprising a two-layer hydrogel. The first layer entraps a GGBP and the second layer comprises a heparin-containing hydrogel. The overall average MPE for the biosensors with the two hydrogel layers was measured at 15.9 (n=37).

In Vivo Glucose Tracking of a Biosensor with a Hydrogel Comprising Methacrylated Heparin The in-vivo performance associated with glucose tracking was equivalent to a non-coated sensor in an environment containing blood. The second coating was applied to a PEG5-SM4 sensor (in a 25 gauge needle) and placed in-vein in a healthy, male Yorkshire swine for about 6 hours. A glucose excursion was performed by administering a 5% glucose solution intravenously. A total of 37 UV coated 2$^{nd}$ layer sensors were tested in-vivo with an average mean percent error (MPE) of 15.9 (standard error=1.74). No fibrin sheaths were observed on the sensor tip and there was no evidence of clot formation on the matrix face. In addition to the MPE being low, the time required for initial equilibrium was low. FIG. 7 includes a sample glucose excursion tracing using a background update as well as the MPE obtained. The sensor, upon removal from the swine, showed no signs of fibrin sheath formation and no evidence of blood clotting (not shown).

What is claimed is:

1. A coated biosensor device comprising at least one coating, wherein the biosensor comprises a protein covalently bound to the coating, wherein the coating comprises a composition comprising a hydrogel matrix, said matrix comprising poly(ethylene glycol) dimethyacrylate with a molecular weight of about 1000 (PEGDMA-1000), 2-hydroxy-2 methyl propiophenone (HMPP) and at least one acrylate, wherein the acrylate is selected from the group consisting of methacrylic acid (MAA) and methyl methacrylate (MMA), wherein the ratio of PEGDMA:Acrylate is from about 10:90 mol % to about 70:30 mol %, and said HMPP is at a concentration of from about 0.2% to about 0.6%, total weight, wherein the composition does not contain hydroxyethyl methacrylate (HEMA) and is cured onto the device, and wherein the coated device is implantable in a subject.

2. The device of claim 1, wherein the ratio of PEGDMA to Acrylate is from about 20:80 mol % to about 25:75 mol %.

3. The device of claim 2, wherein the ratio of PEGDMA to Acrylate is from about 21:79 mol % to about 24:76 mol %.

4. The device of claim 3, wherein the ratio of PEGDMA to Acrylate is from about 22:78 mol % to about 23:77 mol %.

5. The device of claim 4, wherein said HMPP is at a concentration of from about 0.3% to about 0.5%, total weight.

6. The device of claim 5, wherein said HMPP is at a concentration of from about 0.3% to about 0.5%, total weight.

7. The device of claim 6, wherein said HMPP is at a concentration of from about 0.3% to about 0.4%, total weight.

8. The device of claim 1, wherein only one acrylate is present and said acrylate is MAA.

9. The device of claim 1, wherein both MMA and MAA are present.

10. The device of claim 1, wherein said protein is glucose-galactose binding protein.

11. The device of claim 10, wherein the device comprises a needle or cannula.

12. The device of claim 11, further comprising at least a second coating that coats said first coating, said second coating comprising a hydrogel matrix, said matrix comprising poly(ethylene glycol) dimethyacrylate (PEGDMA), 2-hydroxy-2 methyl propiophenone (HMPP), a methacrylated heparin (HP-MA) and at least one acrylate, wherein the acrylate is selected from the group consisting of methacrylic acid (MAA) and methyl methacrylate (MMA), wherein the ratio of PEGDMA to Acrylate to HP-MA is from about 20:25:55 mol % to about 70:15:15 mol %, and said HMPP is at a concentration of from about 0.2% to about 0.6%, total weight.

13. The coated device of claim 12, wherein, in the second coating, the ratio of PEGDMA to Acrylate to HP-MA is from about 55:20:25 mol % to about 30:25:45 mol %.

14. The coated device of claim 13, wherein, in the second coating, the ratio of PEGDMA to Acrylate to HP-MA is about 50:25:25 mol %.

15. A composition comprising a hydrogel matrix, said matrix comprising poly(ethylene glycol) dimethyacrylate (PEGDMA), 2-hydroxy-2 methyl propiophenone (HMPP), a methacrylated heparin (HP-MA) and an acrylate, wherein the acrylate is selected from the group consisting of methacrylic acid (MAA) and methyl methacrylate (MMA), wherein the composition does not contain hydroxyethyl methacrylate (HEMA) and the ratio of PEGDMA to Acrylate to HP-MA is from about 20:25:55 mol % to about 60:25:15 mol %, and said HMPP is at a concentration of from about 0.2% to about 0.6%, total weight.

16. The composition of claim 15, wherein the ratio of PEGDMA to Acrylate to HP-MA is from about 60:25:15 mol % to about 30:25:45 mol %.

17. The composition of claim 16, wherein the ratio of PEGDMA to Acrylate to HP-MA is about 50:25:25 mol %.

18. The composition of claim 15, further comprising a protein.

19. The composition of claim 18, wherein said protein is glucose-galactose binding protein.

20. A coated device comprising at least one coating, wherein the coating comprises the composition of claim 15, wherein the composition is cured onto the device, and wherein the coated device is implantable in a subject.

21. The coated device of claim 20, wherein the device comprises a needle or cannula.

* * * * *